US00PP29215P3

(12) United States Plant Patent
Howell

(10) Patent No.: US PP29,215 P3
(45) Date of Patent: Apr. 10, 2018

(54) APPLE TREE NAMED 'HOWELL TC5 WF'

(50) Latin Name: *Malus Domestica*
Varietal Denomination: Howell TC5 WF

(71) Applicant: William Edward Howell, Prosser, WA (US)

(72) Inventor: William Edward Howell, Prosser, WA (US)

( * ) Notice: Subject to any disclaimer, the term of this patent is extended or adjusted under 35 U.S.C. 154(b) by 0 days.

(21) Appl. No.: 15/530,417

(22) Filed: Jan. 10, 2017

(65) Prior Publication Data

US 2017/0202119 P1 Jul. 13, 2017

Related U.S. Application Data

(60) Provisional application No. 62/388,026, filed on Jan. 12, 2016.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Michelle Bos Legal LLC

(57) ABSTRACT

A new and distinct apple tree is disclosed. 'Howell TC5 WF' is notable for its distinctive bright pink appearance and intense sweet/tart flavor.

2 Drawing Sheets

Latin name of the genus and species of the plant claimed: *Malus Domestica.*
Variety denomination: 'Howell TC5 WF'.

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

The new variety of apple tree 'Howell TC5 WF' was created in the course of a planned breeding program carried out in Prosser, Wash. 'Howell TC5 WF' originated as a result of an open pollination cross in 2001 of 'Cripps Pink' (U.S. Plant Pat. No. 7,197, expired), seed parent, with the pollen parent being 'Honeycrisp' (U.S. Plant Pat. No. 7,197, expired). 'Howell TC5 WF' was selected in 2010 as a single plant from among a population of seedlings derived from the parents, and was selected for the quality of its fruit. It is distinguished from its parents by its bright pinkish red skin and by its intense sweet/tart flavor. Asexual propagation by budding was first carried out in Prosser, Wash. The variety has since been observed over a number of asexually propagated generations, and has been found to remain true to type.

BRIEF SUMMARY OF THE INVENTION

'Howell TC5 WF' is a new and distinct apple tree notable for its distinctive fruit, which has a bright pinkish red skin and an intense sweet/tart flavor.

BRIEF DESCRIPTION OF THE PHOTOGRAPH

DETAILED BOTANICAL DESCRIPTION

Figure 1:
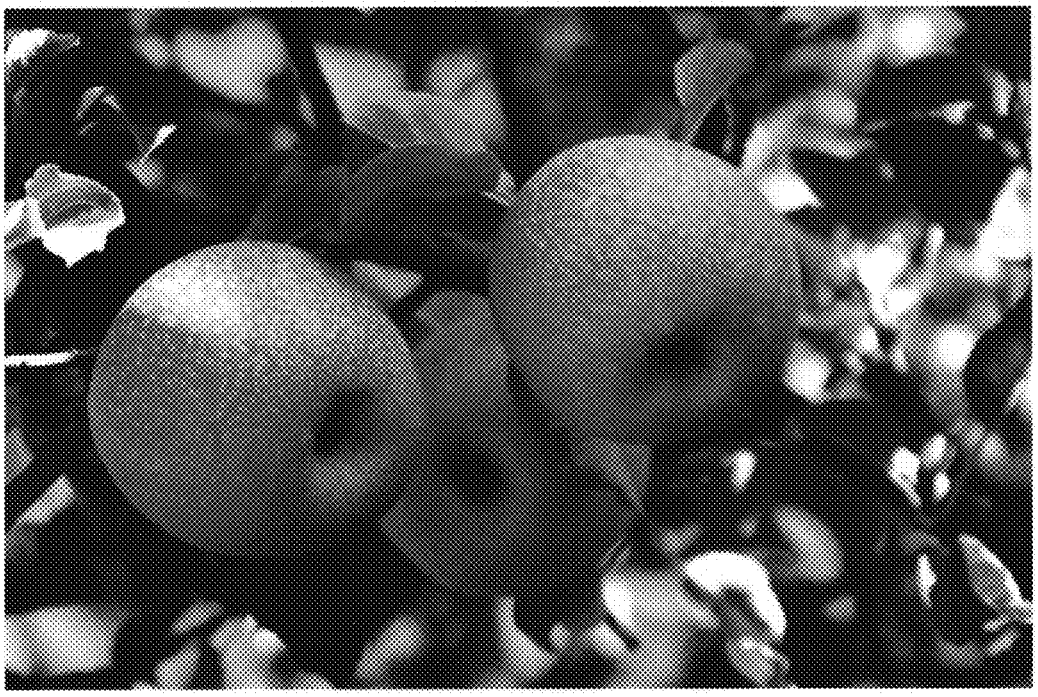
FIG. 1 shows the fruit of the claimed variety on the tree.
Figure 2:
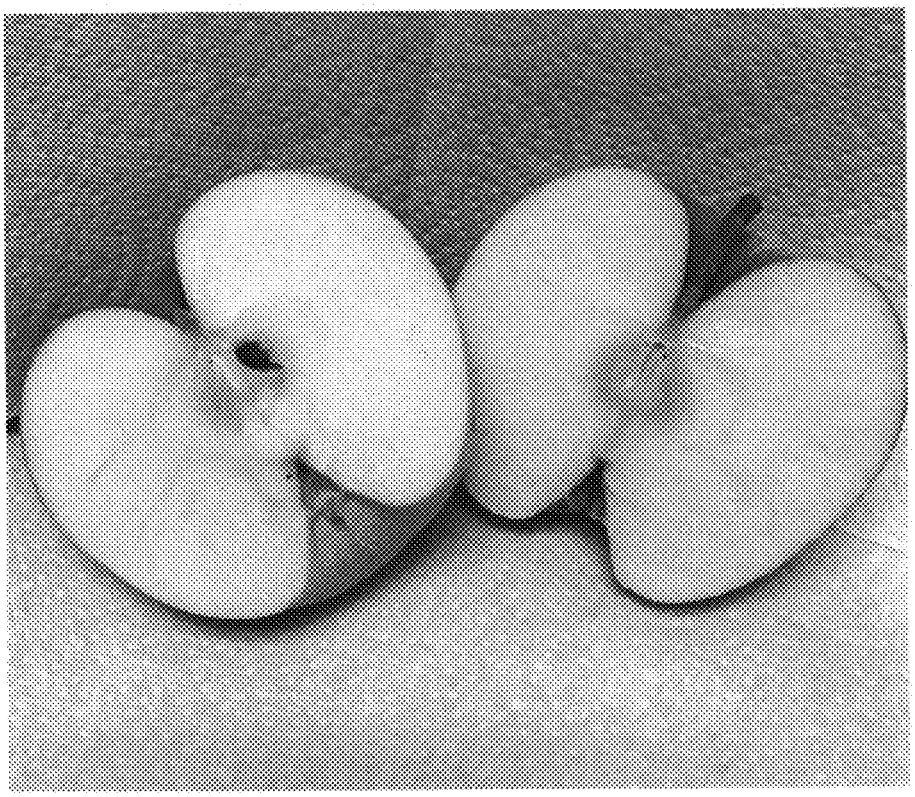
FIG. 2 shows a sectioned fruit of the claimed variety.

The following detailed botanical description is based on observations made during the 2015 growing season at Prosser, Wash. All colors are described according to The Royal Horticultural Society Colour Chart as published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Semi-vigorous.
- *Size.*—Height 2.75 m, spread 1.2 m.
- *Trunk.*—Diameter 2.5 cm at 30 cm above graft union.
- *Bark texture.*—Smooth.
- *Bark coloration.*—Gray to reddish-brown.

Branch:
- *Length.*—Length 81.3 cm.
- *Diameter.*—1.27 cm at 1 m above ground.
- *Crotch angle relative to trunk.*—60°.
- *Color.*—Gray to reddish-brown.

Dormant one-year-old shoot:
- *Size.*—Diameter 1 cm, length 71 cm.
- *Color.*—Gray to reddish-brown.
- *Internode length.*—3.8 cm.

Flowers:
- *Bud quantity per spur.*—4 to 5.
- *Bud shape.*—Cone.
- *Bud length.*—1 cm.
- *Bud diameter.*—0.5 cm.
- *Bud color.*—Greyed-purple 186B.
- *Color at balloon stage.*—Greyed-purple 186C.

*Diameter of open flower.*—4 cm.
*Margin.*—Smooth.
*Relative position of petal margin.*—Overlapping.
*Petal length.*—2 cm.
*Petal width.*—1.4 cm.
*Apex shape.*—Pointed.
*Base shape.*—Pointed.
*Color of upper surface.*—White N155B.
*Color of lower surface.*—White N155C.
*Pistil length.*—0.6 cm.
*Pistil color.*—Yellow 1D.
*Anther quantity.*—14.
*Anther size.*—0.1 cm.
*Color of pollen.*—Yellow 2C.
*Stigma size.*—0.1 cm.
*Stigma color.*—Yellow 2C.
*Style size.*—1 cm.
*Style color.*—1D.
*Ovary width.*—0.3 cm.
*Ovary length.*—0.5 cm.
*Ovary color.*—Yellow-green 146B.
*Bloom period.*—First bloom March 25, full bloom April 3 in Prosser, Wash.

Pedicel:
*Length.*—1.3 cm.
*Diameter.*—0.2 cm.
*Color.*—Yellow-green 145A.

Sepals:
*Quantity.*—5.
*Color.*—Yellow-green 145A.
*Length.*—0.5 cm.
*Width.*—0.4 cm.

Leaf:
*Shape.*—Ovate.
*Attitude in relation to shoot.*—Nearly vertical.
*Blade margin.*—Serrated.
*Apex.*—Acuminate.
*Base shape.*—Rounded.
*Size.*—Length 10.2 cm, width 5.7 cm.
*Color of upper surface.*—Dark green.
*Color of lower surface.*—Green.
*Petiole length.*—2.86 cm.
*Petiole diameter.*—0.32 cm.

Fruit:
*Size.*—Diameter 7.6 cm, height 7.5 cm.
*Weight.*—204 g.
*General shape in profile.*—Rounded.
*Ribbing.*—Absent.
*Crowning at calyx end.*—Moderate.
*Stalk.*—Length 2.5 cm, width 0.3 cm.
*Depth of stalk cavity.*—1.9 cm.
*Width of stalk cavity.*—0.64 cm.
*Size of lenticels.*—0.8 mm.
*Quantity of lenticels.*—Abundant.
*Ground color of skin.*—Yellow.
*Over color of skin.*—Bright pinkish red.
*Pattern of over color.*—Solid flush.
*Flesh.*—Crisp and very juicy.
*Brix.*—15°.
*Quantity of seeds.*—8 to 10 per fruit.
*Shape of seed.*—Acuminate.
*Seed color.*—Dark brown.
*Disease resistance/susceptibility.*—None noted.

Use: Fresh market and processing.

The invention claimed is:

1. I claim a new and distinct apple tree substantially as shown and described herein.

* * * * *